(12) United States Patent
Al-Shammari et al.

(10) Patent No.: US 11,046,627 B2
(45) Date of Patent: Jun. 29, 2021

(54) MTP/MTO TECHNOLOGY PROCESS INTEGRATED FOR PROPYLENE PRODUCTION

(71) Applicant: SABIC Global Technologies B.V., Bergen op Zoom (NL)

(72) Inventors: Talal Al-Shammari, Riyadh (SA); Mohammed Sabri, Riyadh (SA); Hatem Belfadhel, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/342,721

(22) PCT Filed: Oct. 18, 2017

(86) PCT No.: PCT/IB2017/056488
§ 371 (c)(1),
(2) Date: Apr. 17, 2019

(87) PCT Pub. No.: WO2018/083562
PCT Pub. Date: May 11, 2018

(65) Prior Publication Data
US 2020/0039899 A1    Feb. 6, 2020

Related U.S. Application Data

(60) Provisional application No. 62/416,931, filed on Nov. 3, 2016.

(51) Int. Cl.
*C07C 6/04* (2006.01)
*C07C 1/20* (2006.01)
*C07C 11/06* (2006.01)

(52) U.S. Cl.
CPC .............. *C07C 6/04* (2013.01); *C07C 1/20* (2013.01); *C07C 11/06* (2013.01)

(58) Field of Classification Search
CPC ................................. C07C 6/04; C07C 1/20
USPC .................. 585/324, 327, 643, 639, 640
See application file for complete search history.

(56) References Cited

U.S. PATENT DOCUMENTS

| | | |
|---|---|---|
| 8,829,259 B2 | 9/2014 | Bozzano et al. |
| 2008/0154077 A1 | 6/2008 | Bozzano et al. |
| 2011/0112344 A1 | 5/2011 | Chewter et al. |
| 2015/0141605 A1 | 5/2015 | Bradin |

FOREIGN PATENT DOCUMENTS

| | | |
|---|---|---|
| CN | 102190549 B | 7/2014 |
| CN | 103694076 B | 9/2015 |

OTHER PUBLICATIONS

Al Wahabi, Saeed M. "Conversion of Methanol to Light Olefins on SAPO-34 Kinetic Modeling and Reactor Design." Dissertation, Dec. 2003, 167 pages.

Dukandar, Kerman A. "Alternative On-purpose Production Methods for Propylene", CB&I, Global Propylene & Derivatives Summit, 42 pages, 2016.

International Search Report and Written Opinion from PCT/IB2017/056488 dated Feb. 6, 2018, 15 pages.

*Primary Examiner* — Thuan D Dang
(74) *Attorney, Agent, or Firm* — Norton Rose Fulbright US LLP

(57) ABSTRACT

A process for producing propylene from ethylene and butylene using a process that integrates a methanol to propylene (MTP) system or a methanol to olefin (MTO) system with a metathesis reaction system.

6 Claims, 2 Drawing Sheets

MTP/MTO TECHNOLOGY PROCESS INTEGRATED FOR PROPYLENE PRODUCTION

CROSS-REFERENCE TO RELATED APPLICATIONS

This application is a national phase application under 35 U.S.C. § 371 of International Application No. PCT/IB2017/056488 filed Oct. 18, 2017, which claims priority to U.S. Provisional Patent Application No. 62/416,931 filed Nov. 3, 2016. The entire contents of each of the above-referenced disclosures is specifically incorporated by reference herein without disclaimer.

BACKGROUND

Ethylene and propylene (light olefins) are commercially important chemicals that are useful in a variety of processes for making plastics and other chemical compounds. The petroleum and polymer industry is always looking for more efficient ways to produce greater yields of light olefins, and especially propylene, from hydrocarbon feed materials.

The present invention focuses on an improved propylene synthesis process created by integration of a methanol to olefin (MTO) or methanol to propene (MTP) system with a metathesis system.

SUMMARY

Methanol to olefins (MTO) systems produce significant amounts of C2 and C4. Methanol to propene (MTP) systems produce some C2 and C4 as well, but not as much as MTO technologies. In both cases (MTO/MTP) C2 and C4 cuts or fractions can be utilized to maximize overall C3 yield via integrating those technologies with metathesis technology.

Certain embodiments are directed to a process for producing propylene from ethylene and butylene, the process comprising: (a) obtaining from a methanol to propylene (MTP) system or a methanol to olefin (MTO) system a first product stream comprising ethylene and a second product stream comprising butylene; and (b) providing the first and second product streams to a metathesis reaction unit under metathesis reaction conditions sufficient to react the ethylene and butylene to produce a product stream comprising propylene.

Other embodiments are directed to processes for producing propylene from ethylene and butylene, the process comprising: (a) obtaining from a methanol to propylene (MTP) system or a methanol to olefin (MTO) system a first product stream comprising ethylene and a second product stream comprising butylene; (b) providing the first and second product streams to a metathesis reaction unit under metathesis reaction conditions sufficient to react the ethylene and butylene to produce a product stream comprising propylene and unreacted ethylene and butylene; (c) separating the propylene from the unreacted ethylene and butylene; and (d) providing the unreacted ethylene and butylene to the MTP or MTO system.

Still other embodiments are directed to processes for producing propylene from ethylene and butylene, the process comprising: (a) obtaining from a methanol to propylene (MTP) system or a methanol to olefin (MTO) system a first product stream comprising ethylene and a second product stream comprising butylene, wherein the MTP or MTO system comprises: (i) a first reactor that converts methanol to dimethyl ether; and (ii) a second reactor that converts the produced dimethyl ether to a $C_2^+$ product stream comprising propylene, ethylene, and butylene; (b) providing the first and second product streams to a metathesis reaction unit under metathesis reaction conditions sufficient to react the ethylene and butylene to produce a product stream comprising propylene and unreacted ethylene and butylene; (c) separating the propylene from the unreacted ethylene and butylene; and (d) providing the unreacted ethylene and butylene to the MTP or MTO system.

In certain aspects the metathesis reaction can be performed at about 0° C. to 150° C., an absolute pressure of 0.1 to 10 MPa, and/or a weight hourly space velocity (WHSV) from about 1 per hr to about 100 per hr. The butylene in the metathesis feed can be 2-butene. In certain aspects the ratio of C2 to C4 in the metathesis feed source is 0.5, 1, 1.5, 2, 2.5, 3, 4 or more.

In certain aspects the MTO or MTP reactions are performed at a temperature of 300° C. to 700° C. In a particular aspect the MTO or MTP reaction is performed at a temperature of about 500° C. In a further aspect the MTO or MTP reactions are performed at an absolute pressure of 0.1, 0.2, 0.3, 0.4 to 0.5, 0.6, 0.7, 0.8, 0.9, to 1.0 MPa.

In certain aspects propylene product from the MTP system or MTO system is combined with the propylene product of the metathesis system.

In a further aspect the MTO system uses an oxygenate, e.g., methanol as a feed source. In still further aspects the MTP system uses methanol as an feed source and the MTP system is directly integrated with the metathesis system.

The processes described herein can further comprise separating propylene from the ethylene and butylene in the effluent from the MTP or MTO systems.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In the context of the present invention, 15 embodiments are now described. Embodiment 1 is a process for producing propylene from ethylene and butylene. The process included the steps of (a) obtaining from a methanol to propylene (MTP) system or a methanol to olefin (MTO) system a first product stream comprising ethylene and a second product stream containing butylene; and (b) providing the first and second product streams to a metathesis reaction unit under metathesis reaction conditions sufficient to react the ethylene and butylene to produce a product stream containing propylene. Embodiment 2 is the process of embodiment 1, wherein the MTP system uses an oxygenate containing feed source, preferably a methanol containing feed source. Embodiment 3 is the process according to any of embodiments 1 or 2, wherein the metathesis reaction is performed at a temperature between 0° C. and 150° C., preferably 50° C. Embodiment 4 is the process according to any of embodiments 1 to 3, wherein the metathesis reaction is performed at a pressure of 0.1 MPa to 10 MPa. Embodiment 5 is the process according to any of embodiments 1-4, wherein the metathesis reaction is performed at a weight hourly space velocity (WHSV) of 1 to 100 per hour. Embodiment 6 is the process according to any of embodiments 1 to 5, wherein the MTP or MTO process is integrated with the metathesis process.

Embodiment 7 is a process for producing propylene from ethylene and butylene. The process includes the steps of (a) obtaining from a methanol to propylene (MTP) system or a methanol to olefin (MTO) system a first product stream containing ethylene and a second product stream comprising butylene; (b) providing the first and second product streams to a metathesis reaction unit under metathesis reaction conditions sufficient to react the ethylene and butylene to produce a product stream containing propylene and unreacted ethylene and butylene; (c) separating the propylene from the unreacted ethylene and butylene; and (d) providing the unreacted ethylene and butylene to the MTP or MTO system. Embodiment 8 is the process of embodiment 7, wherein the metathesis reaction is performed at a temperature between 0° C. and 150° C., preferably 50° C. Embodiment 9 is the process according to any of embodiments 7 or 8, wherein the metathesis reaction is performed at a pressure of 0.1 MPa to 10 MPa. Embodiment 10 is the process according to any of embodiments 7 to 9, wherein the metathesis reaction is performed at a weight hourly space velocity (WHSV) of 1 to 100 per hour. Embodiment 11 is the process according to any of embodiments 7 to 10, wherein the MTP or MTO process is integrated with the metathesis process.

Embodiment 12 is a process for producing propylene from ethylene and butylene. This process includes the steps of (a) obtaining from a methanol to propylene (MTP) system or a methanol to olefin (MTO) system a first product stream comprising ethylene and a second product stream comprising butylene, wherein the MTP or MTO system includes (i) a first reactor that converts methanol to dimethyl ether; and (ii) a second reactor that converts the produced dimethyl ether to a C2+ product stream comprising propylene, ethylene, and butylene; (b) providing the first and second product streams to a metathesis reaction unit under metathesis reaction conditions sufficient to react the ethylene and butylene to produce a product stream containing propylene and unreacted ethylene and butylene; (c) separating the propylene from the unreacted ethylene and butylene; and (d) providing the unreacted ethylene and butylene to the MTP or MTO system. Embodiment 13 is the process according to embodiment 12, wherein the metathesis reaction is performed at a temperature between 0° C. and 150° C., preferably 50° C. Embodiment 14 is the process according to any of embodiments 12 or 13, wherein the metathesis reaction is performed at a pressure of 0.1 MPa to 10 MPa and a weight hourly space velocity (WHSV) of 1 to 100 per hour. Embodiment 15 is the process according to any of embodiments 12 to 14, wherein the MTP or MTO process is integrated with the metathesis process.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

In certain embodiments of the invention a light olefin source is subjected to metathesis to produce, at least in part, propylene. As used herein, references to "light olefins" are to be understood to generally refer to C2, C3, or C4 olefins, i.e., ethylene, propylene, or butylenes, alone or in combination. In particular, the MTO or MTP reactor produces or results in formation of an MTO or MTP reactor effluent stream that generally comprises fuel gas hydrocarbons such as methane, ethane and propane, light olefins, and C4+ hydrocarbons.

Figure 1:
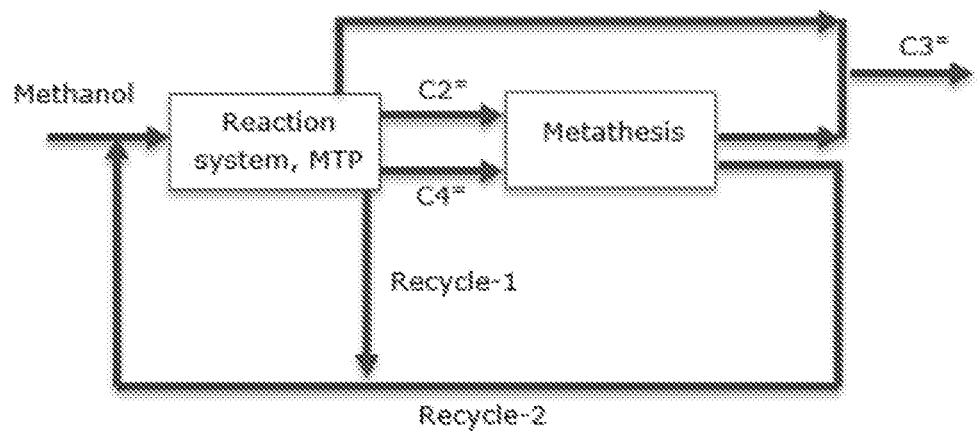
FIG. 1. Illustrates a first scheme for MTP integration with metathesis.

FIG. 1 illustrates a first schematic for one embodiment of an integrated MTP/metathesis system. Methanol feed is introduced into a methanol-to-propylene (MTP) reactor that produces in part an effluent comprising a propylene (C3) product and by-products C2 and C4. The propylene product is separated from the effluent and collected. The C2 and C4 by-products are collected and introduced into a metathesis reactor, while non C3, C2, or C4 products are collected and recycled to the MTP reactor (recycle-1). The metathesis reactor produces an effluent comprising a propylene (C3) product that is separated and collected, and non-propylene by-products that are collected and recycled to the MTP reactor (recycle-2).

Figure 2:
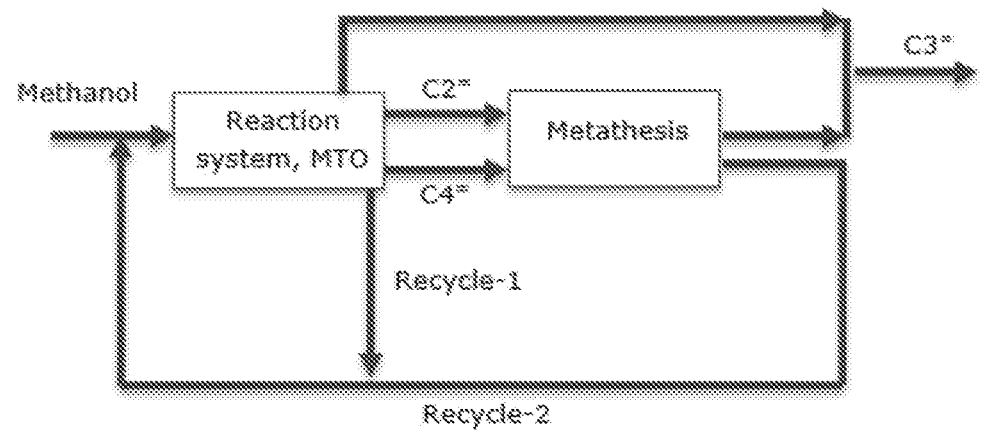
FIG. 2. Illustrates a second scheme for MTO integration with metathesis.

FIG. 2 illustrates a second schematic for one embodiment of an integrated MTO/metathesis system. Methanol feed is introduced into a methanol-to-olefin (MTO) reactor that produces in part an effluent comprising a propylene (C3) product and by-products C2 and C4. The propylene (C3) product is separated from the effluent and collected. The C2 and C4 by-products are collected and introduced into a metathesis reactor, while non C3, C2, or C4 products are collected and recycled to the MTO reactor (recycle-1). The metathesis reactor produces an effluent comprising a propylene (C3) product that is separated and collected, and non-propylene by-products that are collected and recycled to the MTO reactor (recycle-2).

Figure 3:
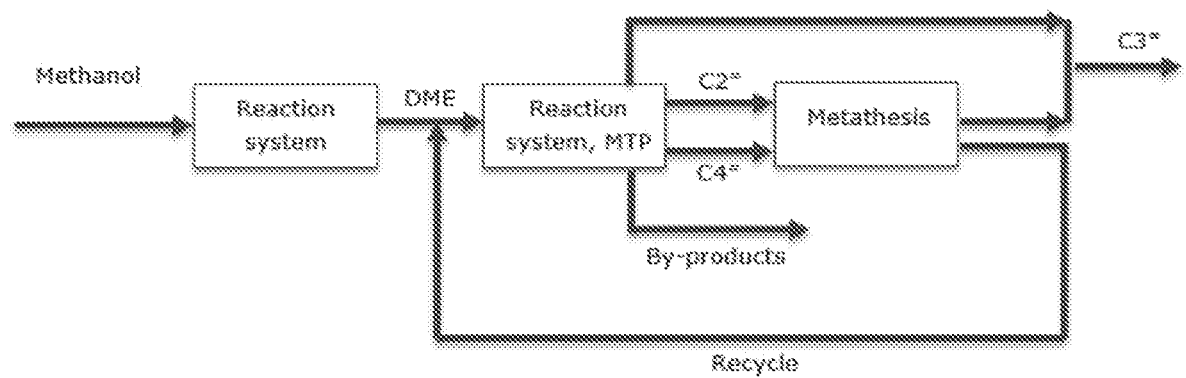
FIG. 3. Illustrates a third scheme for MTP integration with metathesis.

FIG. 3 illustrates a third schematic for one embodiment of an integrated DME/MTP/metathesis system. Methanol feed is introduced into DME producing reactor whose effluent is introduced into a methanol-to-propylene (MTP) reactor that produces in part an effluent comprising a propylene (C3) product and by-products C2 and C4. The propylene (C3) product is separated from the effluent and collected. The C2 and C4 by-products are collected and introduced into a metathesis reactor, while non C3, C2, or C4 products are removed from the system. The metathesis reactor produces an effluent comprising a propylene (C3) product that is separated and collected, and non-propylene by-products that are collected and recycled to the MTP reactor (recycle).

A metathesis reaction is a bimolecular process involving the exchange of bonds between the two reacting chemical species, in particular olefin metathesis is an organic reaction which involves redistribution of olefinic (alkene) bonds. Catalysts for olefin metathesis reactions can include, but are not limited to Group VIA or VIIA metal oxide catalysts, including ruthenium catalysts, such as Grubbs type catalysts, Hoveyda-Grubbs type catalysts, and Indenylidene type catalysts. The light olefin feed source for a metathesis reactor can comprise 20, 30, 40, 50, 60, 70, or 80% C4 hydrocarbons and 80, 70, 60, 50, 40, 30, or 20% C2 hydrocarbons, as well as other components. In certain aspects the C4 hydrocarbon is 20, 30, 40, 50, 60, 70, 80, or 90% butene-1 or butene-2. Products of olefin metathesis reactions can include, but are not limited to, ethylene, acetylene, and propylene. In certain aspects the metathesis reactor is a tube or tube-in-tube reactor. In some aspects, a tube-in-tube reactor can include multiple inner, semi-permeable tubes within an outer reaction tube. Such a multi-inner-semi-permeable tube configuration may be beneficial for industrial production of products and removal of by-products. In certain aspects the tube reactor can be a short reactor with large diameter or a long reactor with small diameter. The temperature of an olefin metathesis reaction can be about 0° C., about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., or between about 0° C. and about 150° C. The reaction can be performed at an absolute pressure of 0.1 to 10 MPa. The weight hourly space velocity (WHSV) can be from about 1 per hr to about 100 per hr. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time.

One source for the light olefin source for the metathesis reaction is an upstream oxygenate to olefins conversion process and specifically the methanol-to-olefins (MTO) process. The MTO process produces light olefins based on converting an oxygenate, such as methanol, ethanol, n-propanol, isopropanol, methyl ethyl ether, dimethyl ether (DME), diethyl ether, di-isopropyl ether, formaldehyde, dimethyl carbonate, dimethyl ketone, acetic acid, and mixtures thereof, and preferably methanol to olefins in the presence of a molecular sieve catalyst. The MTO reaction can include supplying an oxygenate feed, e.g., methanol, and contacting this feed with a molecular sieve catalyst, such as a silicoaluminophosphate (SAPO) molecular sieve catalyst, under conditions designed to convert the oxygenate feed into light olefins. The effluent stream from the MTO reaction can include light olefins as well as methane, ethane, propane, DME, C4 olefins and saturates, C5+ hydrocarbons, water and other hydrocarbon components.

Another source for light olefins is an upstream methanol to propylene (MTP) reaction that includes supplying a methanol feed and contacting this feed with a zeolite catalyst, e.g., HMOR or HZSM-5, under conditions designed to convert the methanol feed into light olefins, particularly propylene.

In certain aspects the MTO or MTP reaction can be performed at a temperature of about 300, 400° C. to 600, 700° C., more particularly at about 500° C., at pressures of 0.1, 0.2, 0.3, 0.4 to 0.5, 0.6, 0.7, 0.8, 0.9, to 1.0 MPa.

The process for converting an oxygenate feed or methanol feed to olefins or propylene can be carried out in a variety of reactors, including as representative examples a fixed bed process, a fluidized bed process, a continuous fluidized bed process, and a continuous high velocity fluidized bed process.

The effluent stream containing a light olefin product can be further processed. For example, the effluent can be directed to a quench unit where the effluent stream is cooled and components condensed. The effluent stream can include one or more of dimethyl ether; C2, C4, C5, and C6 olefins; aromatics; and paraffins. After passing through a separation train that usually includes multiple distillation columns, many of these byproducts are recycled to the MTO or MTP reactor to increase propylene production.

Effluent streams can be passed to one or more quench columns, compressors, or separators. Fractions can be sent to a de-ethanizer, de-propanizer, de-butanizer, or other separation systems. The effluent fraction(s) containing mostly C2 and C4 hydrocarbons can be introduced into a metathesis reactor producing a metathesis reactor effluent (metathesis effluent). The metathesis effluent is separated into a C3 stream and a recycle stream. The recycle stream is sent back to the MTP/MTO reactor or process.

A light olefin-containing effluent stream can be compressed to form a compressed effluent stream. After compression, the compressed stream can be cooled and condensed heavier components of effluent can be collected. The effluent can be further processed and effluent fractions can be collected or processed using one or more method or system to isolate, separate, remove, and/or recycle various components. The light olefins can be recovered as a C2 and/or C4 (C2/C4) olefin stream that has been separated from a C3 olefin stream. The C2/C4 olefin stream can then be processed using the metathesis reaction procedure or reactor for production of C3 olefins. The non-C3 effluent from the metathesis reaction or reactor can be recycled to the feed source of an MTO or MTP reactor.

In further aspects the effluent streams can be passed through one or more heat exchange steps prior to introduction into the reactor in the system.

In certain aspects a light olefin stream can be conditioned to remove acid gases ($CO_2$ and $H_2S$) and dried before further processing. Acid gas removal can be accomplished using a caustic scrubber or similar process or system.

The MTO/MTP effluent stream can be directed to a C2/C3 or a C3/C4 separation system for separating into ethylene and propylene products. The C2/C3 or C3/C4 separation system can include a drier and one or more cryogenic fractionation columns. In certain aspects, other separation processes may be used, including, but not limited to, extractive distillation, selective membrane separation, and/or molecular sieve separation. The present invention is not limited to any particular separation procedure or arrangement.

In one embodiment methanol is used as or included in a feed stream. The feed stream can be introduced in to a DME reactor, which produces a DME reactor effluent stream. DME effluent stream can then be introduced into an MTP reactor producing an MTP effluent stream. The effluent streams can be passed through heat exchange steps prior to introduction into the MTP reactor. Fractions from the effluent streams can be mixed with other recycle streams and returned to the MTP reactor.

The invention claimed is:

1. A process for producing propylene from ethylene and butylene, the process comprising:
  (a) obtaining from a methanol to propylene (MTP) system comprising a zeolite catalyst selected from the group consisting of HMOR and HZSM-5, and a methanol to olefin (MTO) system comprising a silicoaluminophosphate (SAPO) molecular sieve catalyst a first product stream comprising ethylene and a second product stream comprising butylene, wherein the MTP or MTO system comprises:
    (i) a first reactor that converts methanol to dimethyl ether; and
    (ii) a second reactor that converts the produced dimethyl ether to a C2+product stream comprising propylene, ethylene, and butylene;
  (b) providing the first and second product streams to a metathesis reaction unit under metathesis reaction conditions sufficient to react the ethylene and butylene to produce a metathesis product stream comprising propylene and unreacted ethylene and butylene;
  (c) separating the propylene from the unreacted ethylene and butylene in the metathesis product stream to produce a propylene product stream and a stream comprising unreacted ethylene and butylene; and
  (d) providing the stream comprising unreacted ethylene and butylene from step (c) to the MTP or MTO system,
    wherein the metathesis reaction is performed at a temperature between 0° C. and 150° C.;
    wherein the metathesis reaction is performed at a pressure of 0.1 MPa to 10 MPa and a weight hourly space velocity (WHSV) of 1 to 100 per hour; and
    wherein the MTP or MTO system is integrated with the metathesis reaction unit.

2. The process according to claim 1, wherein the MTP system uses an oxygenate containing feed source comprising methanol.

3. The process according to claim 1, wherein the metathesis reaction is performed at a temperature of about 0° C.

4. The process according to claim 1, wherein the metathesis reaction is performed at a temperature of about 20° C.

5. The process according to claim 1, wherein the (MTP) system comprises HMOR as the catalyst.

6. The process according to claim 1, wherein the metathesis reaction is performed at a weight hourly space velocity (WHSV) of 1 per hour.

* * * * *